(12) United States Patent
Srinivasan et al.

(10) Patent No.: US 9,623,194 B2
(45) Date of Patent: Apr. 18, 2017

(54) PASSIVE SAFETY PEN NEEDLE ASSEMBLY

(71) Applicant: Becton, Dickinson and Company, Franklin Lakes, NJ (US)

(72) Inventors: Sudarsan Srinivasan, Wayne, NJ (US); Michael DiBiasi, West Milford, NJ (US); Michael Mochahari, Assam, IN (US); Sajayesh Vijayachandran, Kerala, IN (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 113 days.

(21) Appl. No.: 14/564,813

(22) Filed: Dec. 9, 2014

(65) Prior Publication Data

US 2015/0157808 A1    Jun. 11, 2015

Related U.S. Application Data

(60) Provisional application No. 61/914,306, filed on Dec. 10, 2013.

(51) Int. Cl.
*A61M 5/32* (2006.01)
*A61M 5/34* (2006.01)

(52) U.S. Cl.
CPC .......... *A61M 5/3275* (2013.01); *A61M 5/321* (2013.01); *A61M 5/3202* (2013.01); *A61M 5/3243* (2013.01); *A61M 5/3271* (2013.01); *A61M 5/3293* (2013.01); *A61M 5/343* (2013.01); *A61M 2005/3247* (2013.01);
(Continued)

(58) Field of Classification Search
CPC .. A61M 2005/3254; A61M 2005/3267; A61M 5/321; A61M 5/3243; A61M 5/3271
USPC .................................................. 604/192, 198
See application file for complete search history.

(56) References Cited

U.S. PATENT DOCUMENTS

| 4,894,055 A | 1/1990 | Sudnak |
| 4,897,083 A | 1/1990 | Martell |
| 4,998,924 A | 3/1991 | Ranford |

(Continued)

FOREIGN PATENT DOCUMENTS

| DE | 8909799 U1 | 11/1989 |
| DE | 102006022081 B3 | 1/2008 |

(Continued)

OTHER PUBLICATIONS

Clickfine® AutoProtect™; YPSOMED Selfcare Solutions; www.ypsomed.com/b2b@ypsomed.com.

*Primary Examiner* — Deanna K Hall
(74) *Attorney, Agent, or Firm* — Dickinson Wright PLLC

(57) ABSTRACT

In a first aspect, a safety pen needle assembly is provided herein which includes a hub and a needle fixed to the hub which extends distally from the hub so as to define an injection length. A first shield is slidable relative to the hub from a first state, in which the shield covers at least a substantial portion of the injection length of the needle, to a second state, in which at least a substantial portion of the injection length of the needle is exposed; and, a second shield is slidable from a first position, in which the shield covers the proximal end of the needle, to a second position, in which the proximal end of the needle is exposed. A biasing element is disposed between the first and second shields configured to simultaneously urge the first shield distally and the second shield proximally.

16 Claims, 11 Drawing Sheets

(52) U.S. Cl.
CPC .............. *A61M 2005/3254* (2013.01); *A61M 2005/3267* (2013.01)

(56) References Cited

U.S. PATENT DOCUMENTS

| | | |
|---|---|---|
| 5,061,246 A | 10/1991 | Anapliotis |
| 5,193,552 A | 3/1993 | Columbus et al. |
| 5,246,428 A | 9/1993 | Falknor |
| 5,250,037 A | 10/1993 | Bitdinger |
| 5,256,153 A | 10/1993 | Hake |
| 5,269,765 A | 12/1993 | Kuracina |
| 5,279,579 A | 1/1994 | D'Amico |
| 5,292,314 A | 3/1994 | D'Alessio et al. |
| 5,336,197 A | 8/1994 | Kuracina et al. |
| 5,364,362 A | 11/1994 | Schulz |
| 5,389,085 A | 2/1995 | D'Alessio et al. |
| 5,417,662 A | 5/1995 | Hjertman et al. |
| 5,429,612 A | 7/1995 | Berthier |
| 5,514,097 A | 5/1996 | Knauer |
| 5,562,624 A | 10/1996 | Righi et al. |
| 5,591,138 A | 1/1997 | Vaillancourt |
| 5,609,577 A | 3/1997 | Haber et al. |
| 5,634,906 A | 6/1997 | Haber et al. |
| 5,688,241 A | 11/1997 | Asbaghi |
| 5,795,336 A | 8/1998 | Romano et al. |
| 5,810,775 A | 9/1998 | Shaw |
| 5,873,856 A | 2/1999 | Hjertman et al. |
| 5,971,966 A | 10/1999 | Lav |
| RE36,398 E | 11/1999 | Byrne et al. |
| 5,984,899 A | 11/1999 | D'Alessio et al. |
| RE36,447 E | 12/1999 | Byrne et al. |
| 6,017,329 A | 1/2000 | Hake |
| 6,110,147 A | 8/2000 | Perouse |
| 6,203,529 B1 | 3/2001 | Gabriel et al. |
| 6,224,576 B1 | 5/2001 | Thorne et al. |
| 6,379,336 B1 | 4/2002 | Asbaghi et al. |
| 6,547,764 B2 | 4/2003 | Larsen et al. |
| 6,569,124 B1 | 5/2003 | Perouse |
| 6,692,463 B1 | 2/2004 | Marteau et al. |
| 6,773,415 B2 | 8/2004 | Heiniger |
| 6,796,967 B2 | 9/2004 | Jensen |
| 6,855,129 B2 | 2/2005 | Jensen et al. |
| 6,939,330 B1 | 9/2005 | McConnell-Montalvo et al. |
| 6,986,760 B2 | 1/2006 | Giambattista et al. |
| 7,066,907 B2 | 6/2006 | Crossman et al. |
| 7,074,211 B1 | 7/2006 | Heiniger et al. |
| 7,147,624 B2 | 12/2006 | Hirsiger et al. |
| 7,198,617 B2 | 4/2007 | Millerd |
| 7,229,432 B2 | 6/2007 | Marshall et al. |
| 7,278,986 B1 | 10/2007 | Frost |
| 7,361,160 B2 | 4/2008 | Hommann et al. |
| 7,361,166 B2 | 4/2008 | Bosse et al. |
| 7,370,759 B2 | 5/2008 | Hommann |
| 7,374,558 B2 | 5/2008 | Kirchhofer |
| 7,384,414 B1 | 6/2008 | Marshall et al. |
| 7,442,185 B2 | 10/2008 | Amark et al. |
| 7,540,858 B2 | 6/2009 | DiBiasi |
| 7,635,350 B2 | 12/2009 | Scherer |
| 8,177,745 B2 | 5/2012 | Brechbuehler et al. |
| 2002/0193746 A1 | 12/2002 | Chevallier |
| 2003/0014018 A1 | 1/2003 | Giambattista et al. |
| 2003/0120209 A1 | 6/2003 | Jensen et al. |
| 2004/0122379 A1 | 6/2004 | Bosse et al. |
| 2005/0113750 A1 | 5/2005 | Targell |
| 2005/0267410 A1 | 12/2005 | Koska |
| 2005/0277893 A1 | 12/2005 | Liversidge |
| 2005/0288607 A1 | 12/2005 | Konrad |
| 2006/0095010 A1 | 5/2006 | Westbye |
| 2006/0270984 A1 | 11/2006 | Hommann |
| 2007/0027430 A1 | 2/2007 | Hommann |
| 2007/0129674 A1 | 6/2007 | Liversidge |
| 2007/0156101 A1 | 7/2007 | Liversidge |
| 2007/0173772 A1 | 7/2007 | Liversidge |
| 2007/0255225 A1 | 11/2007 | Alchas et al. |
| 2008/0009807 A1 | 1/2008 | Hommann |
| 2008/0071225 A1 | 3/2008 | Hommann et al. |
| 2008/0077093 A1 | 3/2008 | Gratwohl et al. |
| 2008/0103453 A1 | 5/2008 | Liversidge |
| 2008/0103454 A1 | 5/2008 | Gratwohl et al. |
| 2008/0177237 A1 | 7/2008 | Stonehouse et al. |
| 2008/0249477 A1 | 10/2008 | Paproski et al. |
| 2008/0255526 A1 | 10/2008 | Bosse et al. |
| 2008/0262436 A1 | 10/2008 | Olson |
| 2008/0269691 A1 | 10/2008 | Cowe |
| 2009/0005742 A1 | 1/2009 | Liversidge |
| 2009/0221972 A1 | 9/2009 | Gratwohl et al. |
| 2009/0254042 A1* | 10/2009 | Gratwohl .............. A61M 5/326 604/198 |
| 2009/0259178 A1 | 10/2009 | Bechbuehler et al. |
| 2009/0259196 A1 | 10/2009 | Gratwohl et al. |
| 2010/0114035 A1 | 5/2010 | Schubert et al. |
| 2011/0178473 A1 | 7/2011 | Richards et al. |
| 2011/0257603 A1 | 10/2011 | Ruan et al. |

FOREIGN PATENT DOCUMENTS

| | | |
|---|---|---|
| DE | 102006041810 A1 | 3/2008 |
| EP | 1464353 A1 | 10/2004 |
| EP | 1747789 A2 | 1/2007 |
| FR | 2881053 A1 | 7/2006 |
| WO | 90/02515 A1 | 3/1990 |
| WO | 92/09319 A1 | 6/1992 |
| WO | 92/20281 A1 | 11/1992 |
| WO | 01/91837 A1 | 12/2001 |
| WO | 01/93924 A1 | 12/2001 |
| WO | 03/045480 A1 | 6/2003 |
| WO | 03/105935 A2 | 12/2003 |
| WO | 2004/000397 A1 | 12/2003 |
| WO | 2004030539 A1 | 4/2004 |
| WO | 2004/071560 A1 | 8/2004 |
| WO | 2005/097238 A2 | 10/2005 |
| WO | 2006018626 A1 | 2/2006 |
| WO | 2006/072807 A1 | 7/2006 |
| WO | 2007/077463 A1 | 7/2007 |
| WO | 2008/025179 A1 | 3/2008 |
| WO | 2008/028304 A1 | 3/2008 |
| WO | 2008/028305 A1 | 3/2008 |
| WO | 2008/028312 A1 | 3/2008 |
| WO | 2008/035122 A1 | 3/2008 |
| WO | 2008/043188 A1 | 4/2008 |
| WO | 2008/044067 A1 | 4/2008 |
| WO | 2008/050158 A2 | 5/2008 |
| WO | 2008/083037 A1 | 7/2008 |
| WO | 2009/003300 A1 | 1/2009 |
| WO | 2009/030056 A1 | 3/2009 |
| WO | WO-2009102612 A1 | 8/2009 |
| WO | 2009/114762 A1 | 9/2009 |
| WO | 2010/126432 A1 | 11/2010 |

\* cited by examiner

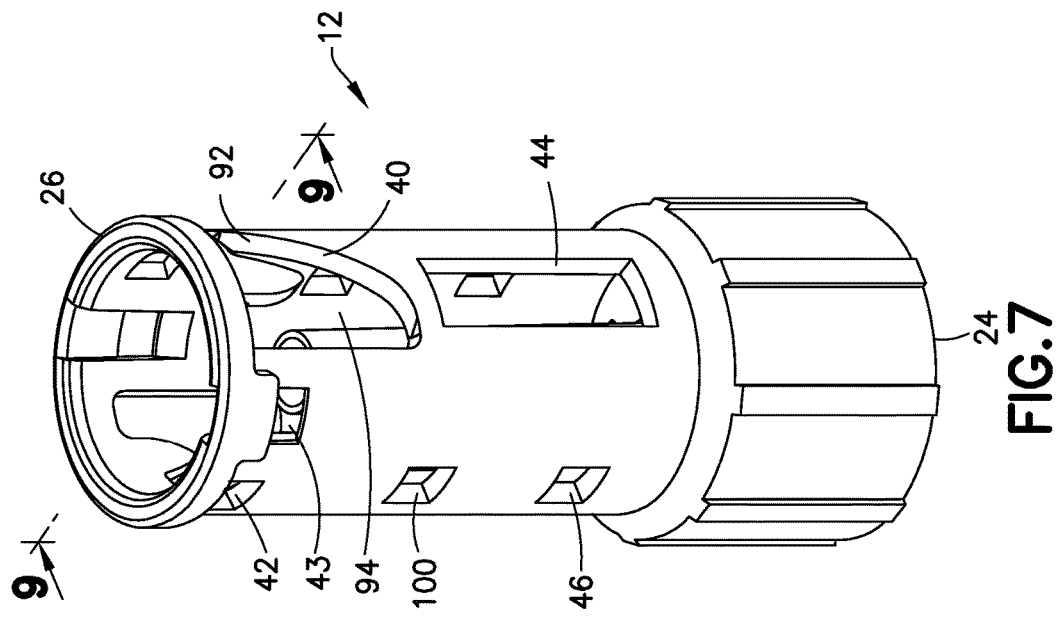
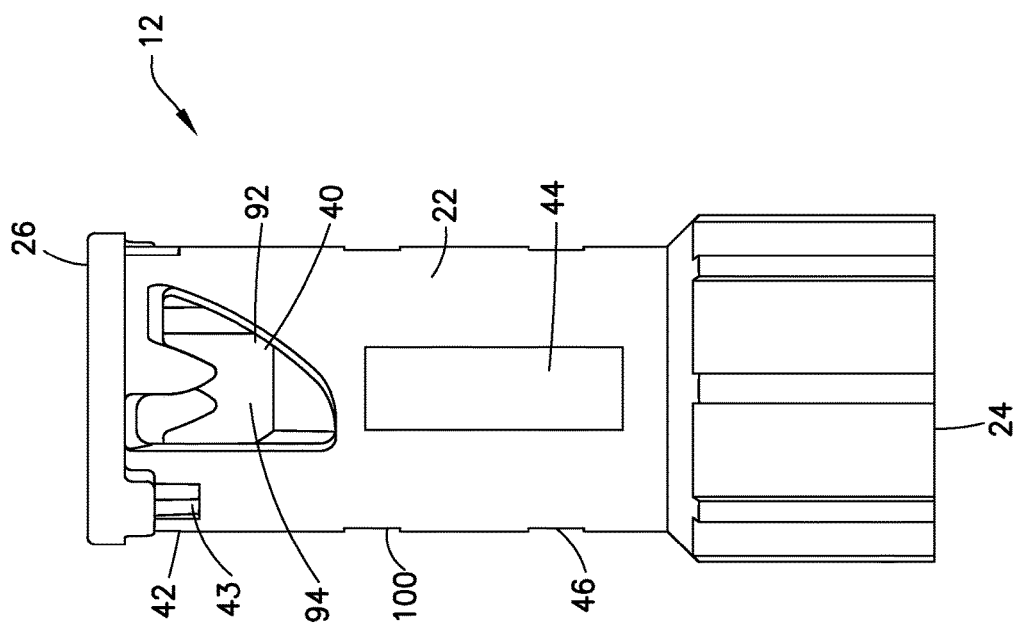

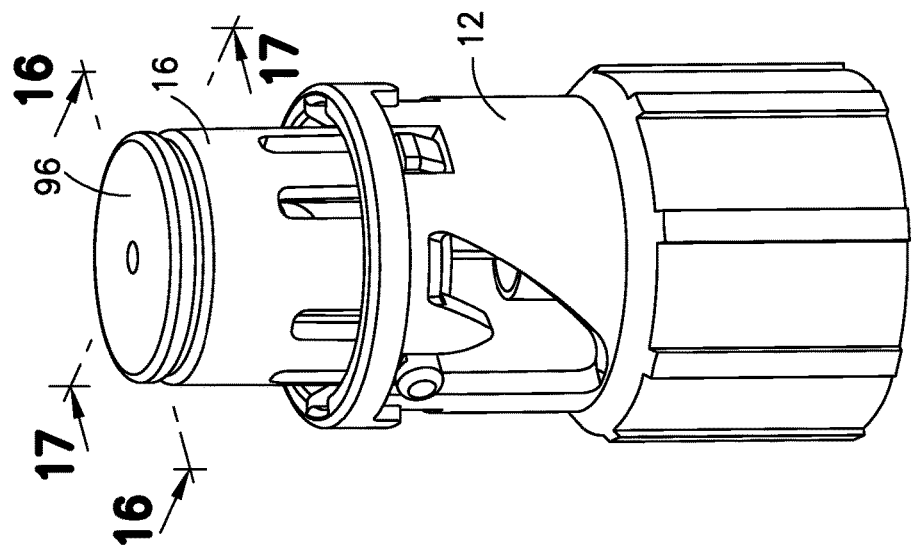
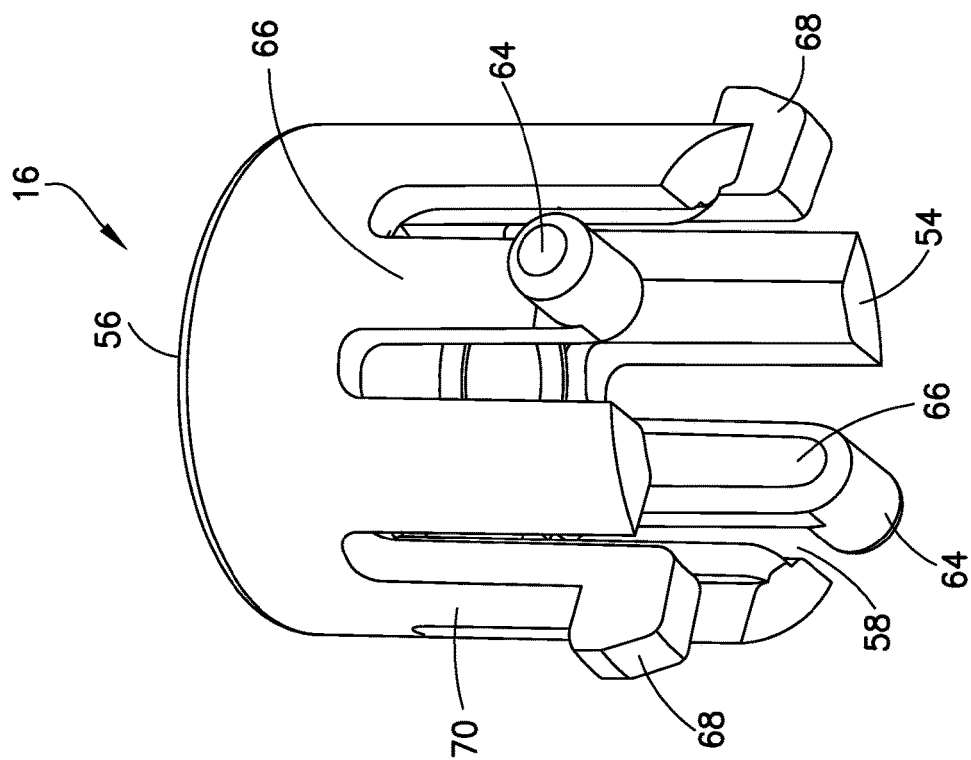
FIG.15
FIG.14

PASSIVE SAFETY PEN NEEDLE ASSEMBLY

CROSS-REFERENCE TO RELATED APPLICATION

This application claims priority to U.S. Provisional Patent Application No. 61/914,306, filed Dec. 10, 2013, the entire contents of which are hereby incorporated by reference.

BACKGROUND OF THE INVENTION

Safety pen needle assemblies are known in the prior art for shielding a used needle post-injection. Such assemblies may be generally classified as "passive" or "active". A passive device is typically considered to be one where shielding may be achieved without requiring additional steps beyond that required to conduct an injection. In contrast, an active device is typically considered to be one where shielding requires one or more additional steps beyond that required to conduct an injection, such as, for example, triggering a spring-fired shield.

In addition, shielding is most commonly utilized with the distal, patient end of the needle. Shielding has been also provided for the proximal, non-patient end of the needle and has been provided on the same device for both the distal and proximal ends of the needle post-injection. U.S. Pat. No. 7,540,858 to DiBiasi and U.S. Published Patent Application No. 2011/0178473 A1 to Richards et al., both to the assignee herein, show passive dual end shielding safety pen needle assemblies where both the distal and proximal ends of the needle may be shielded passively post-injection.

SUMMARY OF THE INVENTION

In a first aspect, a safety pen needle assembly is provided herein which includes a hub having a proximal end and a distal end, and a needle fixed to the hub, the needle having a distal end, formed for insertion into a patient, and a proximal end. The needle extends distally from the distal end of the hub so as to define an injection length of the needle between the distal end of the needle and the distal end of the hub. The assembly further includes a first shield slidable relative to the hub from a first state, in which, the shield covers at least a substantial portion of the injection length of the needle, to a second state, in which at least a substantial portion of the injection length of the needle is exposed. Further, a second shield is provided slidable relative to the hub from a first position, in which the shield covers the proximal end of the needle, to a second position, in which the proximal end of the needle is exposed. A biasing element is disposed between the first and second shields configured to simultaneously generate a biasing force configured to urge the first shield distally towards the first state and to generate a biasing force configured to urge the second shield proximally towards the first position. Advantageously, a passive safety pen needle assembly may be formed which requires a minimal number of parts.

In a further aspect, a safety pen needle assembly is provided utilizing only the patient end shield of the subject invention.

These and other features of the invention will be better understood through a study of the following detailed description and accompanying drawings.

BRIEF DESCRIPTION OF THE DRAWINGS

FIGS. 1-14 show an embodiment of a passive safety pen needle assembly, and components thereof, formed in accordance with the subject invention; and, FIGS. 15-17 show a further embodiment of a passive safety pen needle assembly, and components thereof, formed in accordance with the subject invention.

DETAILED DESCRIPTION OF THE INVENTION

Figure 1:
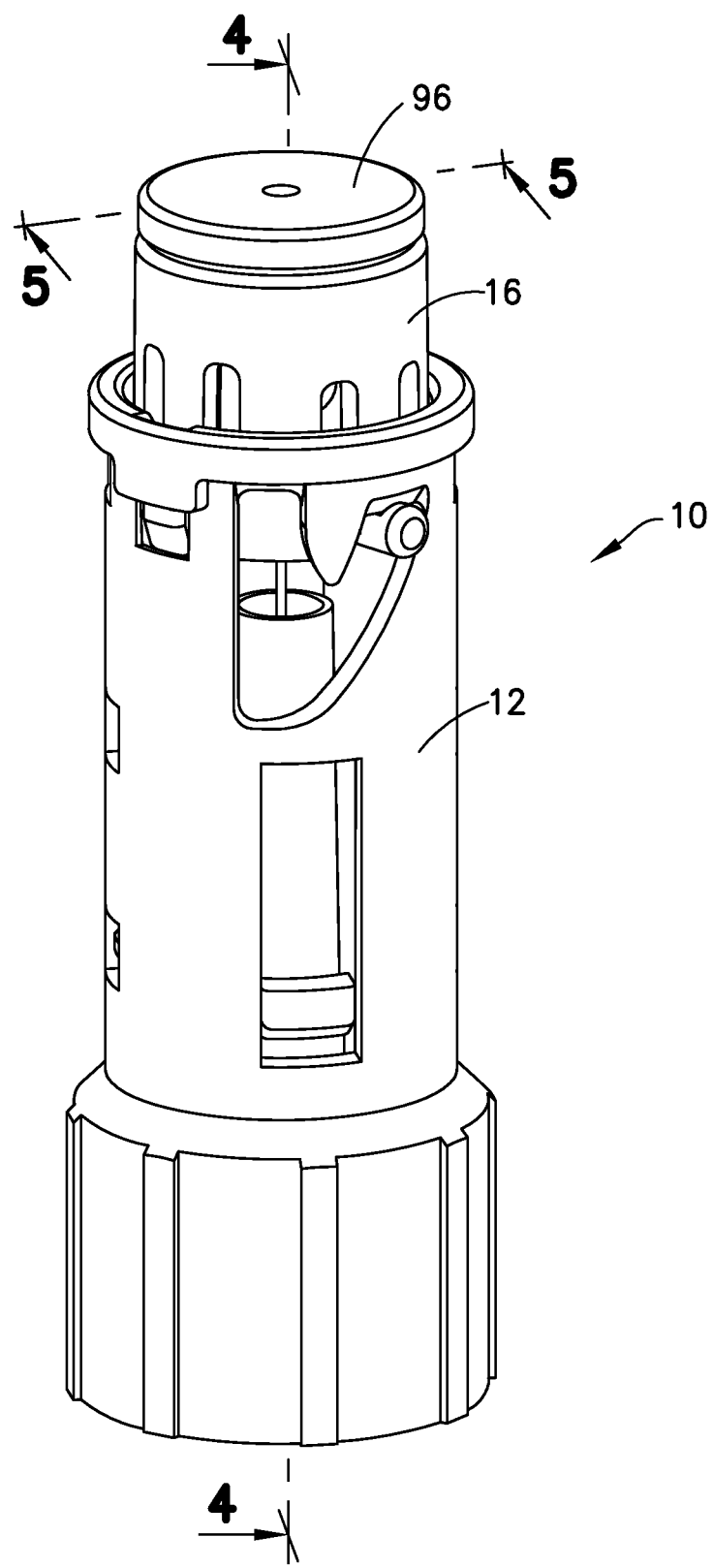

With reference to FIGS. 1-14, a safety pen needle assembly 10 is shown which generally includes a hub 12, a needle 14, a first shield 16, a second shield 18 and a biasing element 20. As will be appreciated by those skilled in the art, the safety pen needle assembly 10 is usable with various medical injectors, but is particularly well-suited for use with medical pen injectors.

As used herein the term "distal", and derivatives thereof, refer to a direction generally towards a patient, while the term "proximal", and derivatives thereof, generally refer to a direction away from a patient.

With specific reference to FIGS. 6-9, the hub 12 includes tubular outer wall 22 which extends between proximal and distal ends 24, 26. A passageway 28 extends between the proximal and distal ends 24, 26 with a cross-piece 30 extending across a portion thereof. Columnar support 32 extends from the cross-piece 30 with a passage 34 extending therethrough configured to receive and support the needle 14 in a fixed state. One or more openings 36 are formed through the cross-piece 30.

Mounting feature 38 may be defined on the interior of the outer wall 22 in proximity to the proximal end 24. The mounting feature 38 may be any known feature usable for mounting the safety pen needle assembly 10 onto a medical injector, such as a thread, bayonet-lock feature, a surface configuration (e.g., a tapered or Luer surface) and so forth. The cross-piece 30 is preferably located distally of the mounting feature 38.

At least one guide slot 40 is formed in the outer wall 22 in proximity to the distal end 26. In addition, at least one locking aperture 42 is provided in proximity to each guide slot 40. It is further preferred that at least one channel 44 be located in the outer wall 22 distally of the cross-piece 30. Further, at least one retention aperture 46 is preferably formed in the outer wall 22 distally of the cross-piece 30.

The needle 14 includes a distal end 48, which is formed for insertion into a patient, and a proximal end 50. The needle 14 is fixed inside the passage 34, using any known technique, such as with adhesive, fusion, etc., so that the distal end 48 of the needle 14 is located distally of the distal end 26 of the hub 12, so as to define an injection length I (FIG. 4), and the proximal end 50 of the needle 14 is located proximally of the cross-piece 30. Preferably, the proximal end 50 of the needle 14 is located distally of the proximal end 24 of the hub 12. The needle 14 is of any configuration whereby liquid may be conveyed between the distal and proximal ends 48, 50, e.g., having a cannula configuration.

Figure 13:
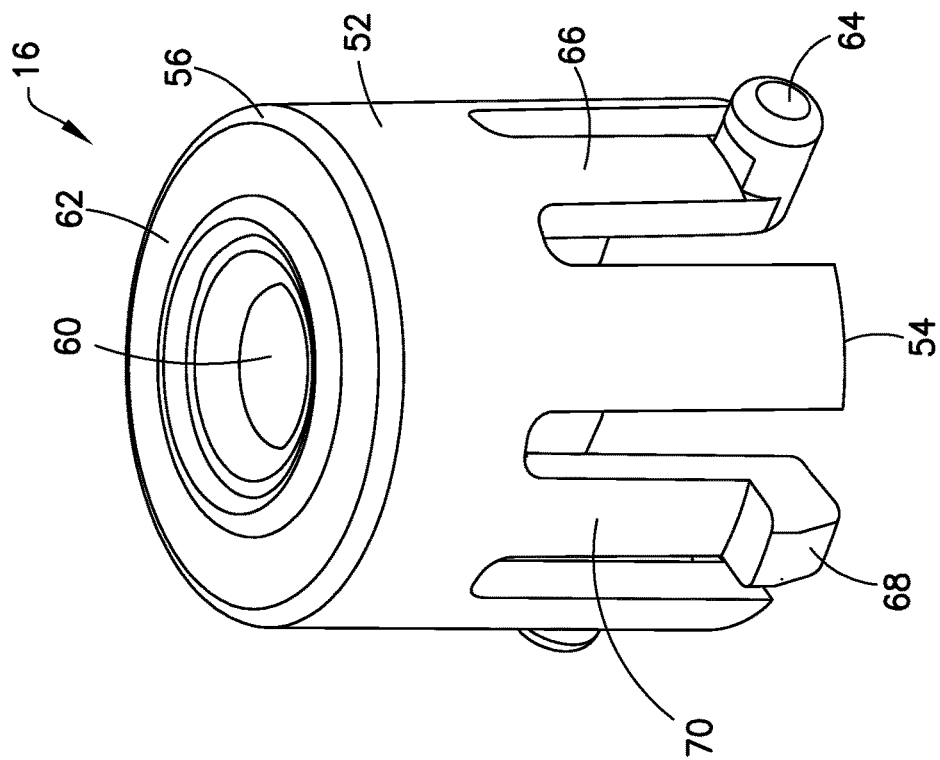

With reference to FIGS. 13 and 14, the first shield 16 includes a generally tubular body 52 having proximal and distal ends 54, 56. A proximal opening 58 is defined at the proximal end 54 and a distal opening 60 is defined at the distal end 56. Optionally, a covering wall 62 may be provided to extend between the distal opening 60 and the distal end 56 of the body 52. The proximal and distal openings 58, 60 are configured to permit passage therethrough of the needle 14.

Figure 4:
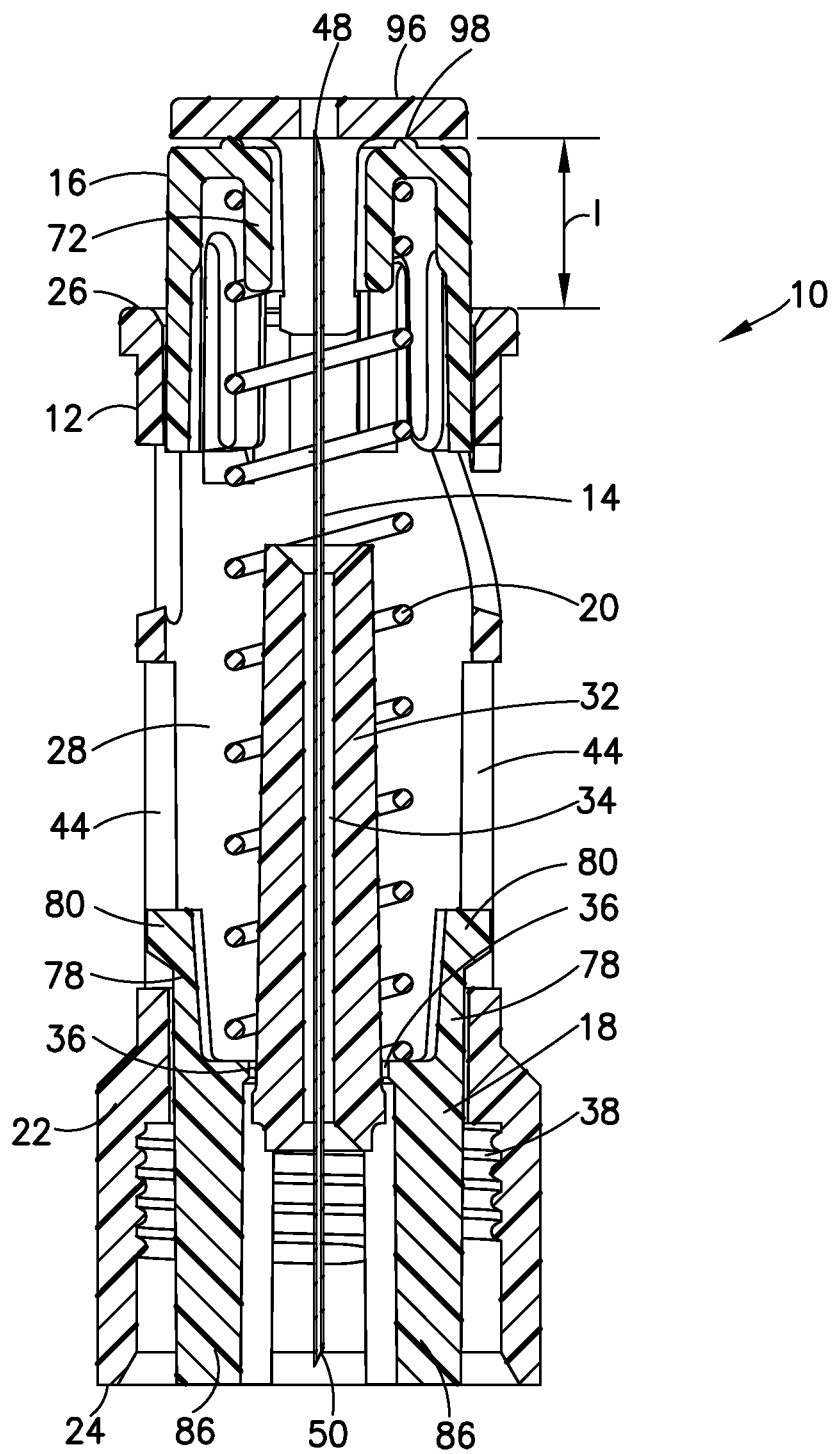

The first shield 16 is provided with at least one guide protrusion 64. The guide protrusion 64 is formed to be seatingly received within the guide slot 40. Portions of the body 52 about the guide protrusion 64 may be removed so as to define a cantilevered arm 66 on which the guide protrusion 64 is located. In addition, at least one locking tab 68 is provided on the first shield 16 configured to be snap engaged in the locking aperture 42. It is preferred that the body 52 provide sufficient resilience to maintain snap engagement with the locking tab 68 received in the locking aperture 42. To this end, the constituent material of the body 52 may provide such resiliency. In addition, or alternatively, the locking tab 68 may be located on cantilevered locking arm 70. As best shown at FIG. 4, a mounting collar 72 may be provided to extend proximally from the covering wall 62.

Figure 11:
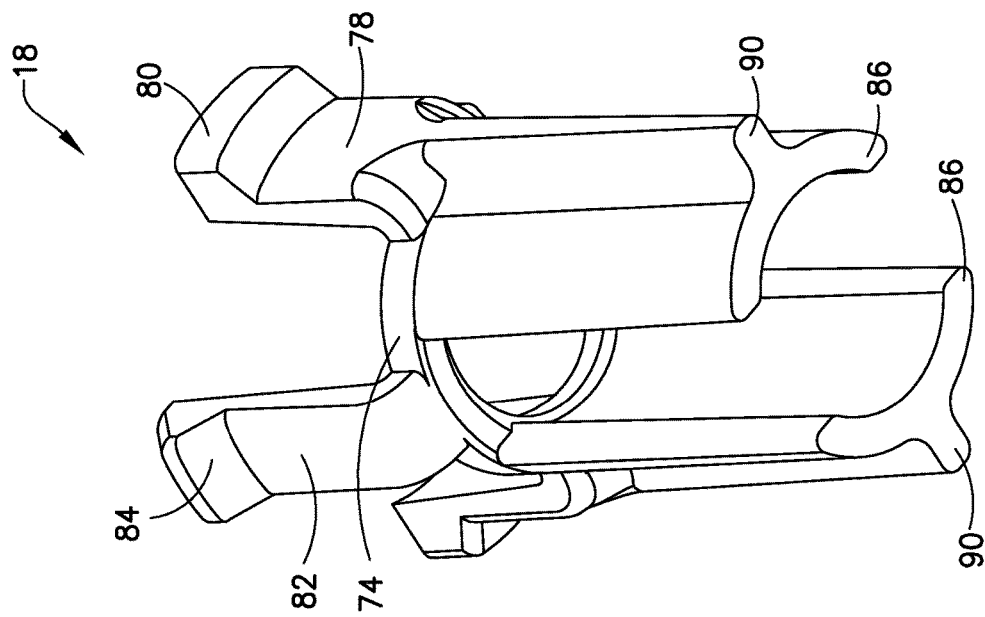
Figure 10:
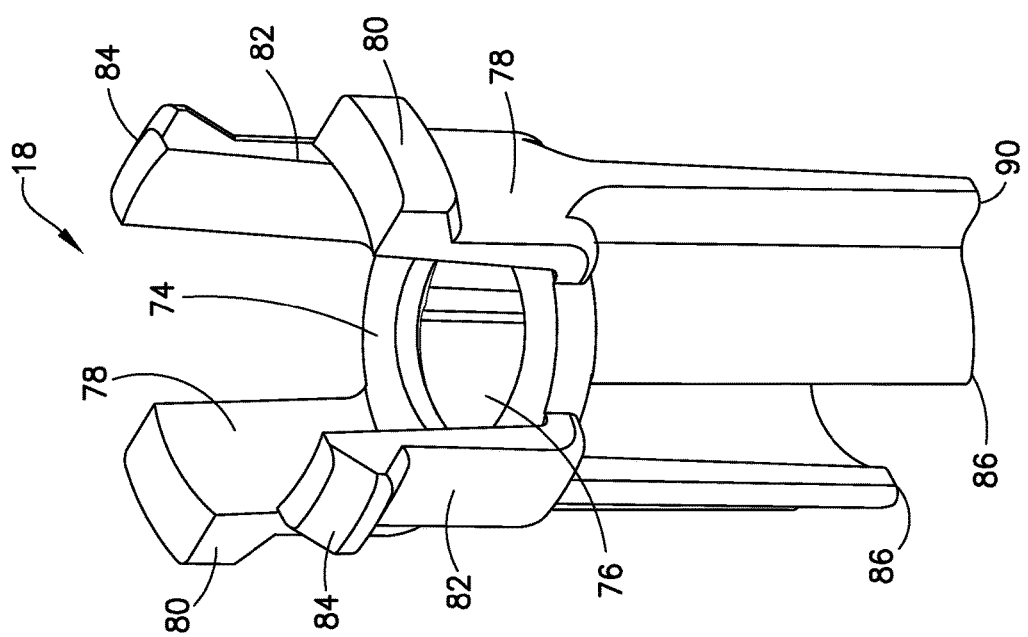
Figure 12:
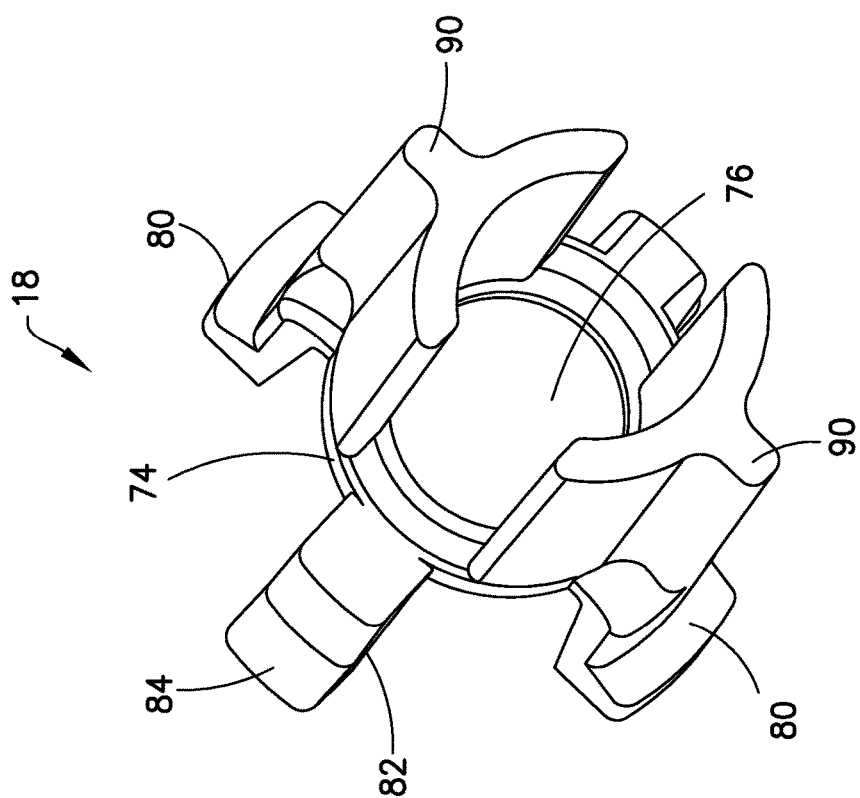

With reference to FIGS. 10-12, the second shield 18 includes a base 74 having an opening 76 defined therein sized to permit passage therethough of the needle 14. At least one guide arm 78 extends distally from the base 74 having an enlarged portion 80 extending therefrom. The enlarged portion 80 is sized to be received in the channel 44 in sliding engagement. In addition, at least one locking arm 82 extends distally from the base 74 having a locking detent 84 defined thereon. At least one shield members 86 extends proximally from the base 74. It is preferred that at least two of the shield members 86 be provided to define a relatively enclosed circumference. The shield members 86 are formed to pass through the openings 36 formed in the cross-piece 30. To allow for stable sliding movement of the shield members 86 through the openings 36, the openings 36 may be provided with cut-outs 88 formed to receive corresponding ridges 90 which extend radially outwardly form the shield members 86.

Figure 5:
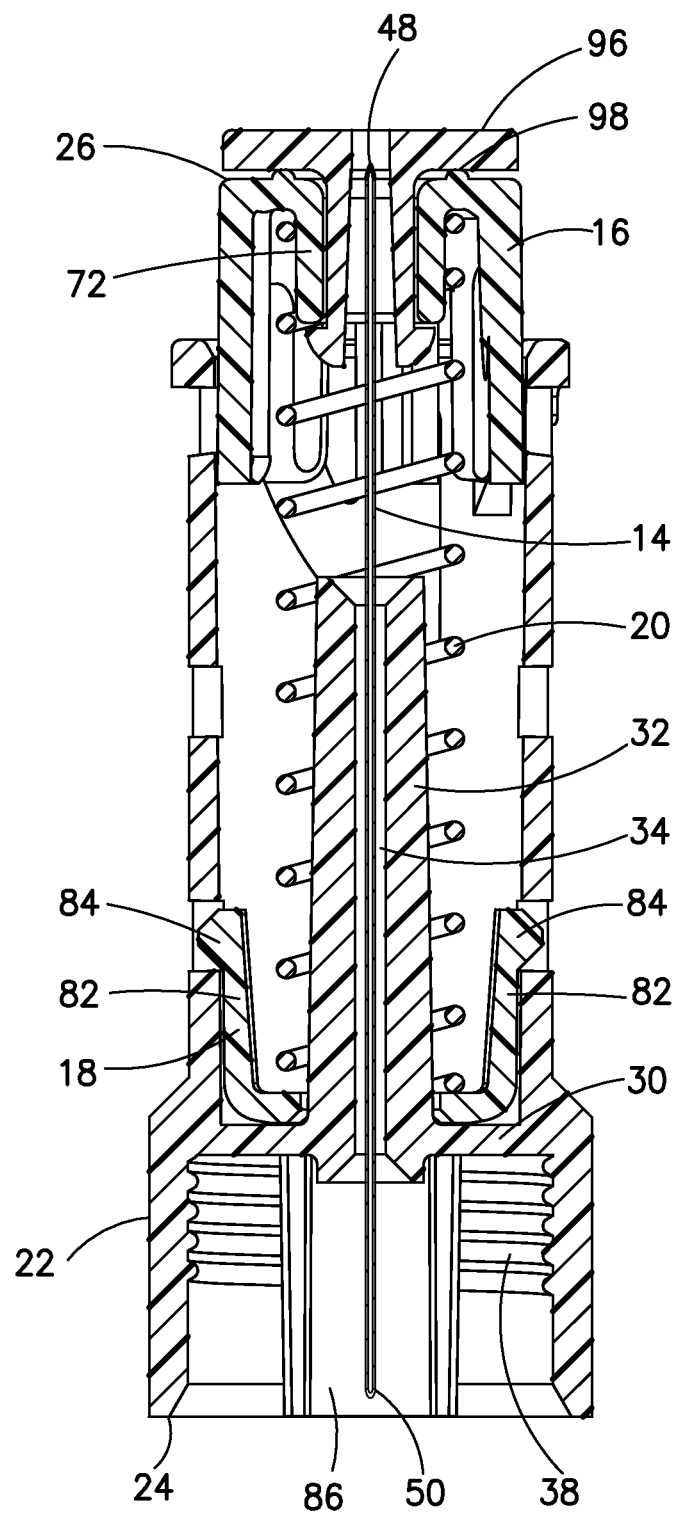
Figure 9:
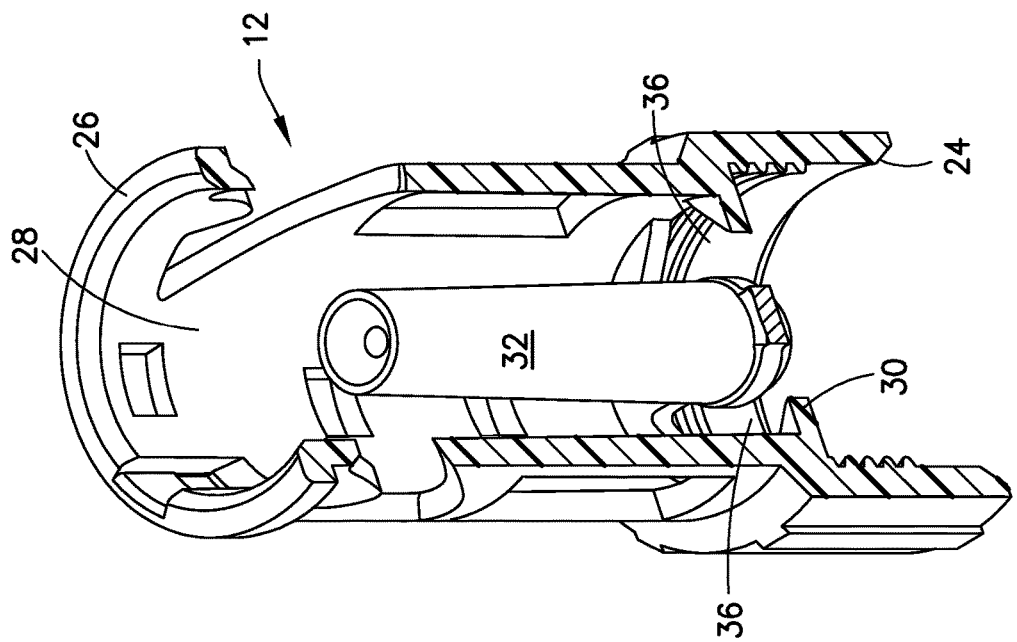
Figure 8:
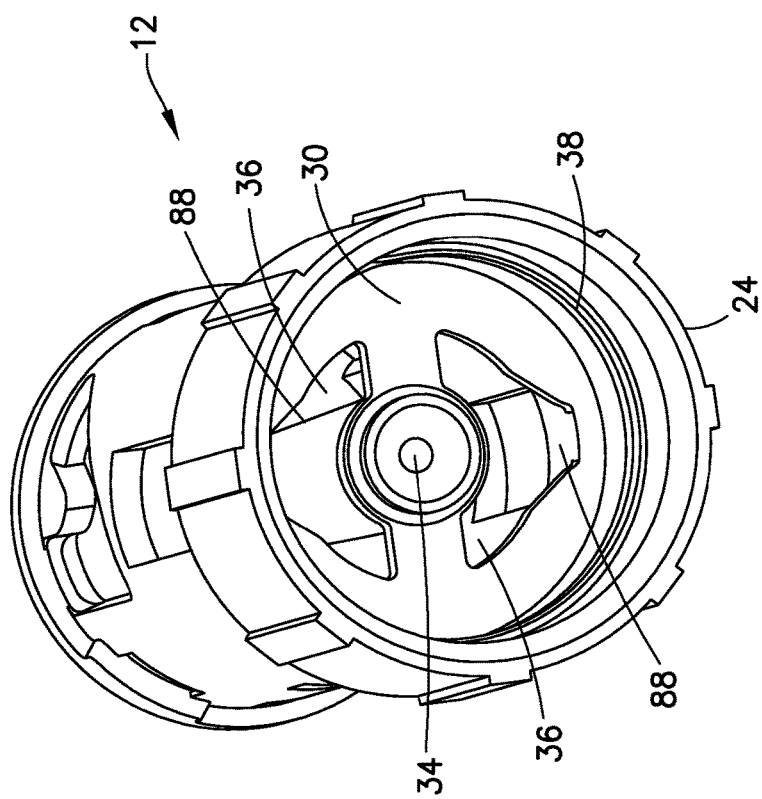

The biasing element 20 is preferably a single component, such as a spring, e.g., a coil or a compression spring. The biasing element 20, as shown in FIGS. 4 and 5, is located within the hub 12 between the first and second shields 16, 18. It is preferred that the support 32 extend through a portion of the biasing element 20 so as to provide columnar support therefor against buckling of the biasing element 18 when compressed during use. In addition, the mounting collar 72 may extend through a portion of the biasing element 20 to provide additional columnar support.

The biasing element 20 is configured to simultaneously generate biasing force configured to distally urge the first shield 16 and to proximally urge the second shield 18.

In an initial state, as shown in FIGS. 1-5, the first shield 16 is located to cover at least a substantial portion of the injection length I of the needle 14. A substantial portion is considered herein to be at least half the injection length I. The distal end 48 of the needle 14 may be initially exposed to permit visual access for priming and insertion into a patient.

Figure 2:
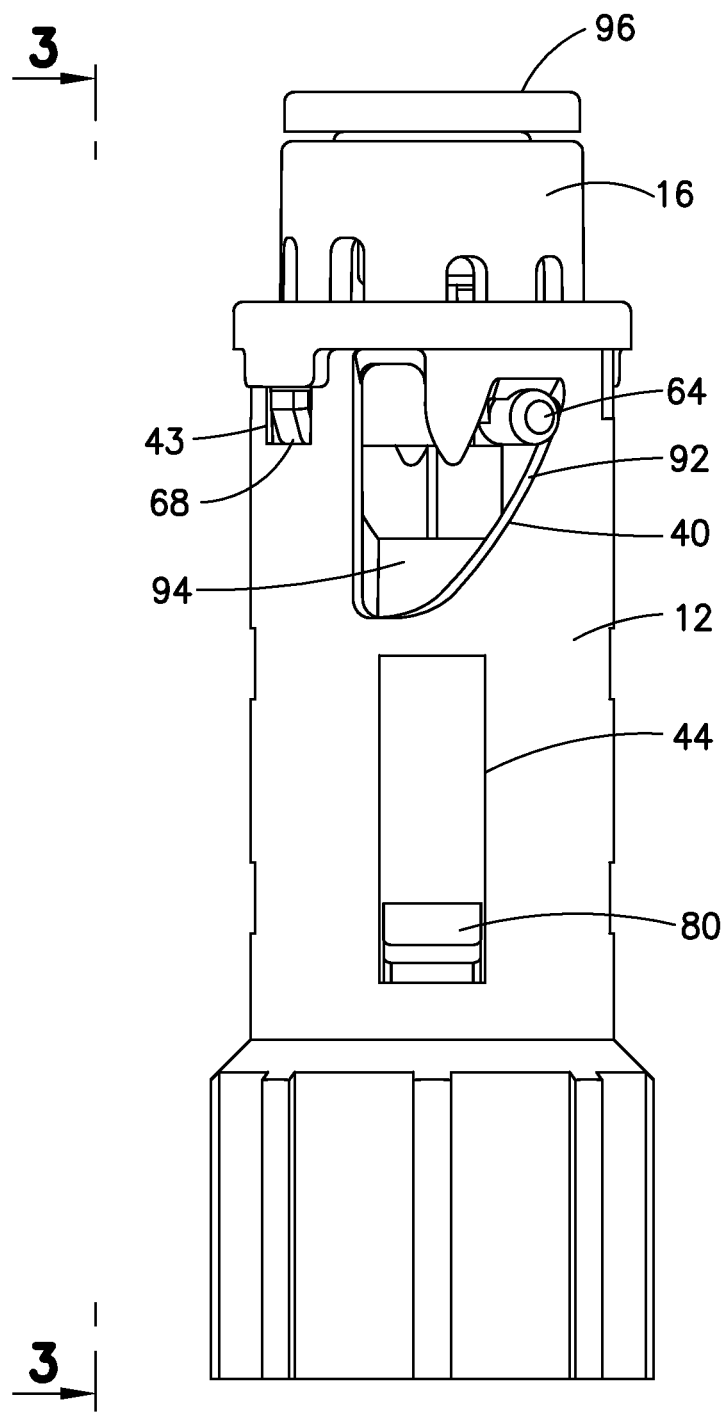
Figure 3:
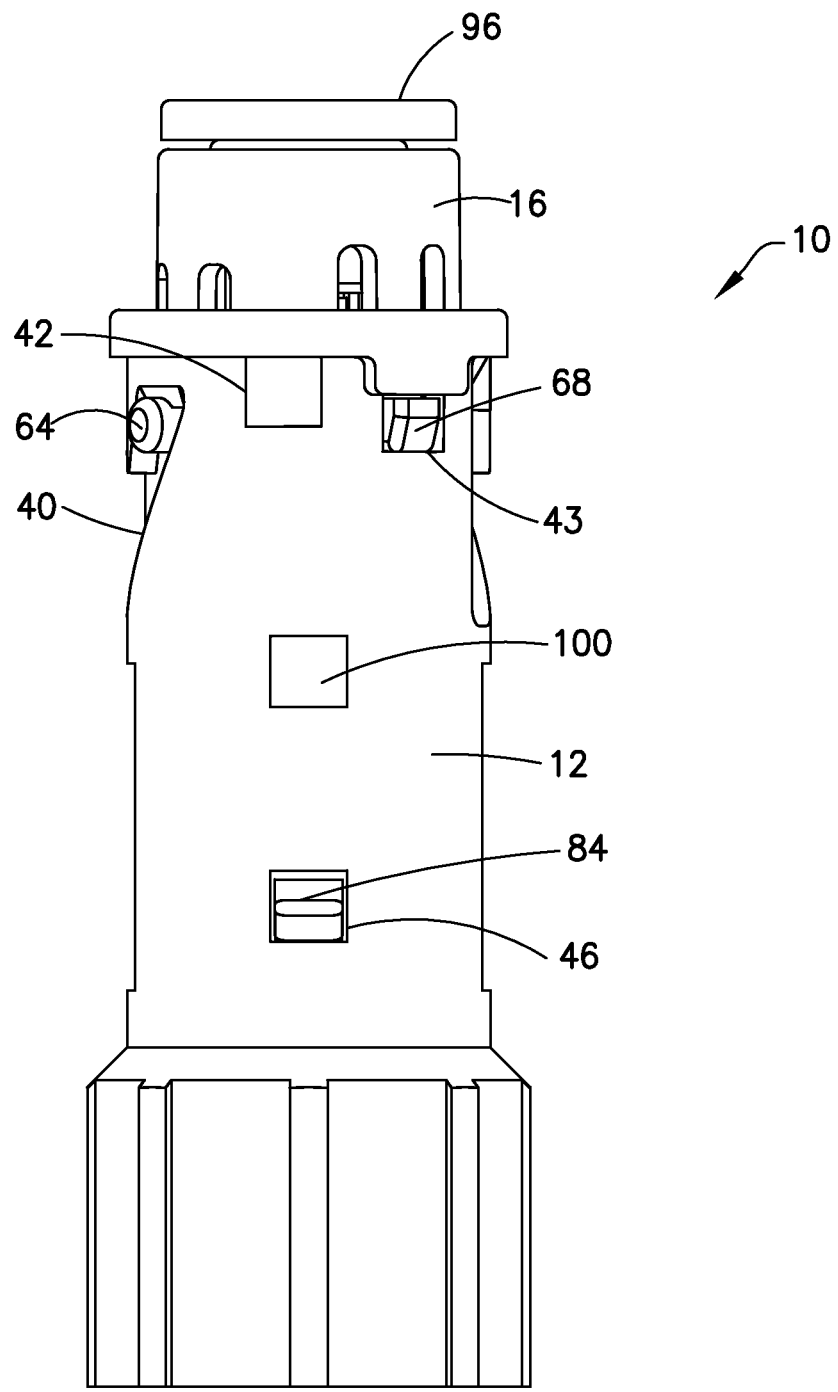

As shown in FIG. 2, in the initial state, the guide protrusion 64 is received in the guide slot 40. Preferably, the guide slot 40 has a first portion 92 which is disposed at an angle relative to the longitudinal axis of the hub 12. In addition, the guide slot 40 includes a second portion 94 in communication with and extending from the first portion 92. The second portion 94 is preferably parallel to the longitudinal axis of the hub 12. With the safety pen needle assembly 10 being mounted into a medical injector, such as with the mounting feature 38, and with the needle 14 being properly primed, the first shield 16 is caused to be pressed against a patient's skin and with force applied to the safety pen needle assembly 10, the first shield 16 is caused to be displaced proximally so as to expose at least a substantial portion of the injection length of the needle 14. With proximal movement of the first shield 16, the guide protrusion 64 is caused to traverse the first portion 92 of the guide slot 40 resulting in rotation of the first shield 14 and ultimate alignment of the guide protrusion 64 in the second portion 94 of the guide slot 40. Proximal retraction of the first shield 16 causes the biasing element 20 to be compressed inside the hub 12. With removal of the first shield 16 from the patient's skin after injection, the biasing element 20 urges the first shield 16 distally towards a shielding state. Due to rotation of the first shield 16, the locking tab 68 is axially aligned with the locking aperture 42 so as to be received in snap engagement therewith with the first shield 16 being in a state at least substantially covering the injection length of the needle 14. In an initial state, the locking tab 68 may be located in a storage aperture 43 prior to rotation of the first shield 16. The snap engagement of the locking tab 68 in the locking aperture 42 locks the first shield 16 in the shielding state.

It is noted that the first shield 16 may be caused to cover the distal end 48 of the needle. As shown in the Figures, a rotatable skin engagement member 96 may be provided such as that disclosed in U.S. Published Patent Application No. 2012/0046614 A1, which is incorporated by reference herein. As shown in FIG. 4, the rotatable skin engagement member 96 may cover the distal end 48 of the needle 14 with the first shield 16 being in the final shielding locked state. In any regard, the first shield 16 covers at least a substantial portion of the injection length I of the needle 14 in the shielding state. It is also noted that the rotatable skin engagement member 96 may be formed to engage the mounting cover 72 for rotation. Further, a bead 98 may be formed on the covering wall 62 to engage the rotatable skin engagement member 96 in minimizing friction between the first shield 16 and the rotatable skin engagement member 96.

In addition, in an initial state, as shown in FIGS. 4 and 5, the second shield 18 may cover the proximal end 50 of the needle 14. With mounting of the safety pen needle assembly 10 onto a medical injector, the second shield 18 is urged distally against force of the biasing element 20. In moving distally, the shield members 86 slide within the openings 36. As shown in FIG. 2, the enlarged portion 80 is disposed within the channel 44. With distal movement of the second shield 18, channel 44 guides the enlarged 80 axially, preferably parallel to the longitudinal axis of the hub 12. This helps to maintain radial alignment of the second shield 18 relative to the hub 12.

Upon removal of the safety pen needle assembly 10 from a medical injector, the biasing element 20 urges the second shield 18 proximally towards a shielding state. The enlarged portion 80 slides along the channel 44 during such movement. The second shield 18 may be configured to engage the cross-piece 30 to limit proximal movement of the second shield 18 coincident with the shielding state in which the second shield 18 covers the proximal end 50 of the needle 14. In the shielding state, the locking detent 84 may be positioned to be snap engaged in the retention aperture 46 so as to inhibit further distal movement of the second shield 18 relative to the hub 12.

A secondary retention aperture 100 may be provided to receive the locking detent 84 in snap engagement during use. Preferably, this snap engagement is overcome by the force of the biasing element 20, particularly with the biasing element being compressed during use by the distal retraction of second shield 18 relative to the hub 12. The compressive force of the biasing element 20 may be further increased due to the proximal retraction of the first shield 16 relative to the hub 12 during use.

As will be appreciated by those skilled in the art, advantageously, the biasing element 20, acting alone, may be used with the subject invention to passively cause shielding of both the distal and proximal ends 48, 50 of the needle 14.

This allows for a minimal number of parts to be used to provide a passive safety pen needle assembly capable of shielding both ends of a needle.

Figure 16:
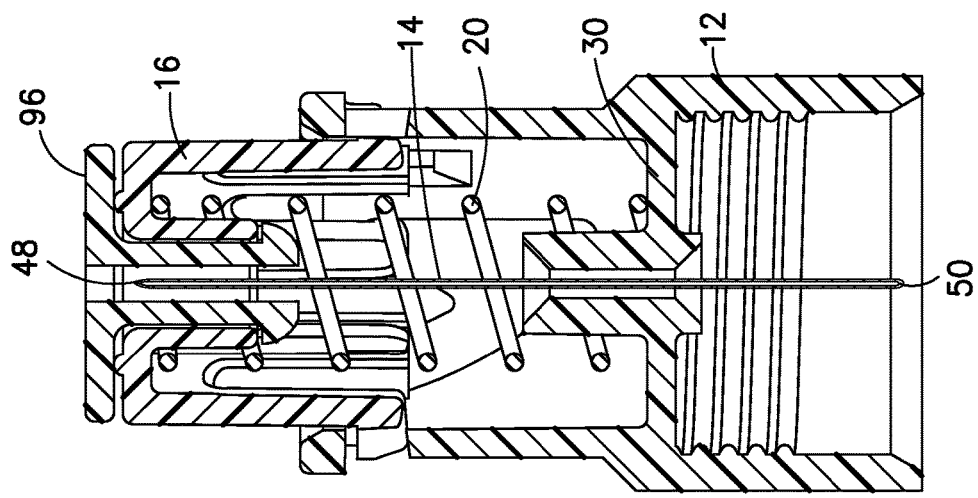
Figure 17:
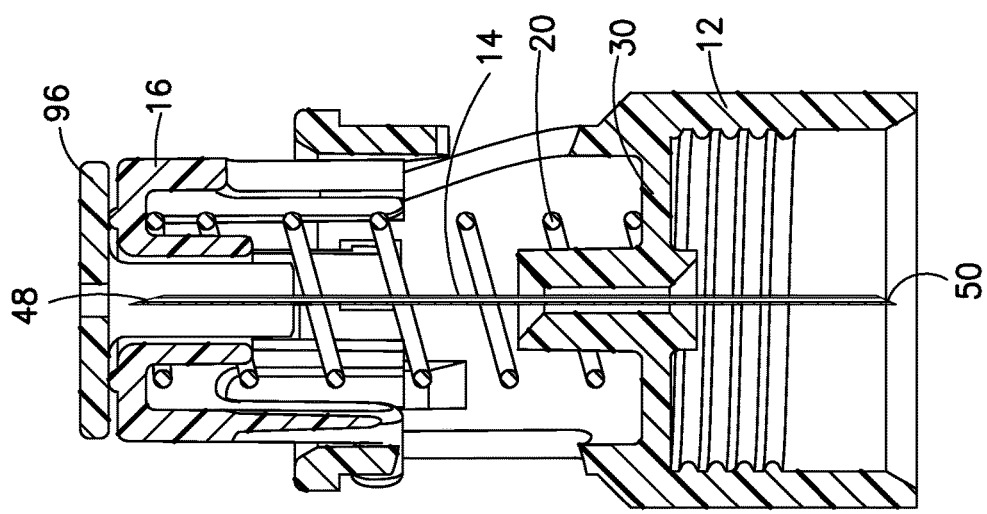

As a further variation of the subject invention, and with reference to FIGS. 15-17 the safety pen needle assembly 10 may be modified to only use the first shield 16 for shielding the distal end 48 of the needle 14 without use of the second shield 18. In this embodiment, biasing element 20 is positioned to act against the cross-piece 30, rather than the second shield 18.

What is claimed is:

1. A safety pen needle assembly comprising:
   a hub having a proximal end and a distal end and a cross piece between said proximal end and said distal end forming one or more openings through the cross piece;
   a needle fixed to said hub, said needle having a distal end, formed for insertion into a patient, and a proximal end, said needle extending distally from said distal end of said hub so as to define an injection length of said needle between said distal end of said needle and said distal end of said hub;
   a first shield slidable relative to said hub from a first state, in which said first shield covers at least a substantial portion of said injection length of said needle, to a second state, in which at least a substantial portion of said injection length of said needle is exposed;
   a second shield slidable relative to said hub from a first position, in which said shield covers said proximal end of said needle, to a second position, in which said proximal end of said needle is exposed, said second shield having a base positioned on a distal side of said cross piece, said base having one or more shield members extending proximally from said base through said one or more openings in said cross piece, and one or more locking arms extending from a distal side of said base, said one or more locking arms configured to mate with said hub to retain said second shield in said second position; and,
   a biasing means disposed between said first and second shields configured to simultaneously generate a biasing force configured to urge said first shield distally towards said first state and to generate a biasing force configured to urge said second shield proximally towards said first position.

2. A safety pen needle assembly as in claim 1, wherein said biasing means is a single spring.

3. A safety pen needle assembly as in claim 1, wherein said biasing means is in pressing engagement with said first shield and with said second shield.

4. A safety pen needle assembly as in claim 1, wherein a mounting feature is provided on said hub configured to mount the safety pen needle assembly onto a medical injector.

5. A safety pen needle assembly as in claim 4, wherein, with mounting of the safety pen needle assembly onto a medical injector, said second shield is urged distally towards said second position against force of said biasing means.

6. A safety pen needle assembly as in claim 5, wherein, upon removal of the safety pen needle assembly from the medical injector, said biasing means urges said second shield proximally towards said first position.

7. A safety pen needle assembly as in claim 1, wherein said biasing means is located distally of said cross-piece.

8. A safety pen needle assembly as in claim 1, wherein said at least one shield member of said second shield extending through said openings cover said proximal end of said needle with said second shield being in said first position.

9. A safety pen needle assembly of claim 1, wherein said second shield has one or more guide arms extending from said distal side of said base, said guide arms configured for sliding engagement with said hub.

10. A safety pen needle assembly of claim 1, wherein said one or more locking arms has a locking detent for locking with a recess in said hub.

11. A safety pen needle assembly of claim 9, wherein said one or more guide arms has an enlarged portion for sliding in a longitudinally extending opening of said hub.

12. A safety pen needle assembly of claim 1, wherein said base of said second shield has an opening for receiving a portion of said hub in sliding engagement.

13. A safety pen needle assembly comprising:
    a hub having a proximal end and a distal end;
    a needle fixed to said hub, said needle having a distal end, formed for insertion into a patient, and a proximal end, said needle extending distally from said distal end of said hub so as to define an injection length of said needle between said distal end of said needle and said distal end of said hub;
    a first shield slidable relative to said hub from a first state, in which said first shield covers at least a substantial portion of said injection length of said needle, to a second state, in which at least a substantial portion of said injection length of said needle is exposed;
    a second shield slidable relative to said hub from a first position, in which said shield covers said proximal end of said needle, to a second position, in which said proximal end of said needle is exposed, said second shield having a base with a distal side and a guide arm extending from said distal side for sliding in a longitudinal opening in said hub to limit rotational movement of said second shield relative to said hub, and a proximal side having one or more shield members extending from said proximal side to cover said proximal end of said needle; and,
    a biasing member disposed between said first and second shields configured to simultaneously generate a biasing force configured to urge said first shield distally towards said first state and to generate a biasing force configured to urge said second shield proximally towards said first position.

14. The pen needle assembly of claim 13, wherein said second shield further includes at least one locking arm extending from said distal side of said base and configured to engage said hub to lock said second shield in said first position and in said second position.

15. The pen needle assembly of claim 14, wherein said hub includes a first aperture for receiving said locking arm when said second shield is in said first position and a second aperture for receiving said locking arm when said second shield is in said second position.

16. The pen needle assembly of claim 14, wherein said locking arm having a locking detent configured for being received in said first aperture and said second aperture of said hub.

* * * * *